(12) United States Patent
Krause

(10) Patent No.: US 10,883,532 B2
(45) Date of Patent: Jan. 5, 2021

(54) FLEXIBLE SHAFT FOR USE AS AN INTERNAL SPLINT FOR INDUSTRIAL APPLICATION

(71) Applicant: William R. Krause, Charlottesville, VA (US)

(72) Inventor: William R. Krause, Charlottesville, VA (US)

(*) Notice: Subject to any disclaimer, the term of this patent is extended or adjusted under 35 U.S.C. 154(b) by 0 days.

(21) Appl. No.: 16/155,362

(22) Filed: Oct. 9, 2018

(65) Prior Publication Data
US 2019/0120282 A1  Apr. 25, 2019

Related U.S. Application Data

(63) Continuation-in-part of application No. 15/445,168, filed on Feb. 28, 2017, now abandoned, which is a continuation-in-part of application No. 13/830,379, filed on Mar. 14, 2013, now Pat. No. 9,579,132.

(51) Int. Cl.
| | |
|---|---|
| A61B 17/72 | (2006.01) |
| F16C 1/04 | (2006.01) |
| F16B 7/18 | (2006.01) |
| A61B 17/74 | (2006.01) |
| F16C 1/06 | (2006.01) |
| F16C 1/08 | (2006.01) |

(52) U.S. Cl.
CPC ............ *F16C 1/04* (2013.01); *A61B 17/72* (2013.01); *A61B 17/7208* (2013.01); *A61B 17/742* (2013.01); *F16B 7/18* (2013.01); *F16C 1/06* (2013.01); *F16C 1/08* (2013.01); *F16C 2226/76* (2013.01); *F16C 2226/78* (2013.01); *F16C 2316/10* (2013.01)

(58) Field of Classification Search
CPC . A61B 17/72; A61B 17/7208; A61B 17/7216; A61B 17/7225; A61B 17/7233; A61B 17/7241; A61B 17/725; A61B 17/7258; A61B 17/7266; A61B 17/7275; A61B 17/7283; A61B 17/7291; A61B 17/846; A61B 17/86
See application file for complete search history.

(56) References Cited

U.S. PATENT DOCUMENTS

| 5,643,258 A | 7/1997 | Robioneck et al. |
| 6,053,922 A | 4/2000 | Krause et al. |
| 6,322,591 B1 | 11/2001 | Ahrens |

(Continued)

FOREIGN PATENT DOCUMENTS

RU  2334580  9/2008

*Primary Examiner* — Si Ming Ku
(74) *Attorney, Agent, or Firm* — Kimberly O Snead

(57) ABSTRACT

A flexible connecting rod is manufactured from a rigid material and having a substantially cylindrical hollow body, a leading segment with a securing area and a trailing segment having a trailing edge and a securing area. The body has at least one flexible center section, each having at least one slot to provide flexibility. The slot follows a sinuous, serpentine path to form a plurality of interlocking teeth that can follow a helical or a concentric path. Each slot has a proximal end spaced from the trailing segment and a distal end spaced from the leading segment. With multiple slots the proximal end of a slot can be spaced from, and separated by an inflexible section, or adjacent to, a distal end of a subsequent slot.

13 Claims, 22 Drawing Sheets

(56) References Cited

U.S. PATENT DOCUMENTS

| | | |
|---|---|---|
| 6,503,249 B1 | 1/2003 | Krause et al. |
| 2005/0277936 A1 | 12/2005 | Siravo et al. |
| 2007/0173834 A1 | 7/2007 | Thakkar |
| 2008/0183170 A1 | 7/2008 | Metzinger et al. |
| 2008/0057868 A1 | 9/2008 | Stoneburner et al. |
| 2009/0177240 A1 | 7/2009 | Perez |
| 2010/0134078 A1 | 6/2010 | Murakami et al. |
| 2011/0144703 A1* | 6/2011 | Krause ............... A61B 17/8625 606/309 |
| 2011/0295252 A1* | 12/2011 | Tipirneni ............. A61B 17/861 606/62 |

* cited by examiner

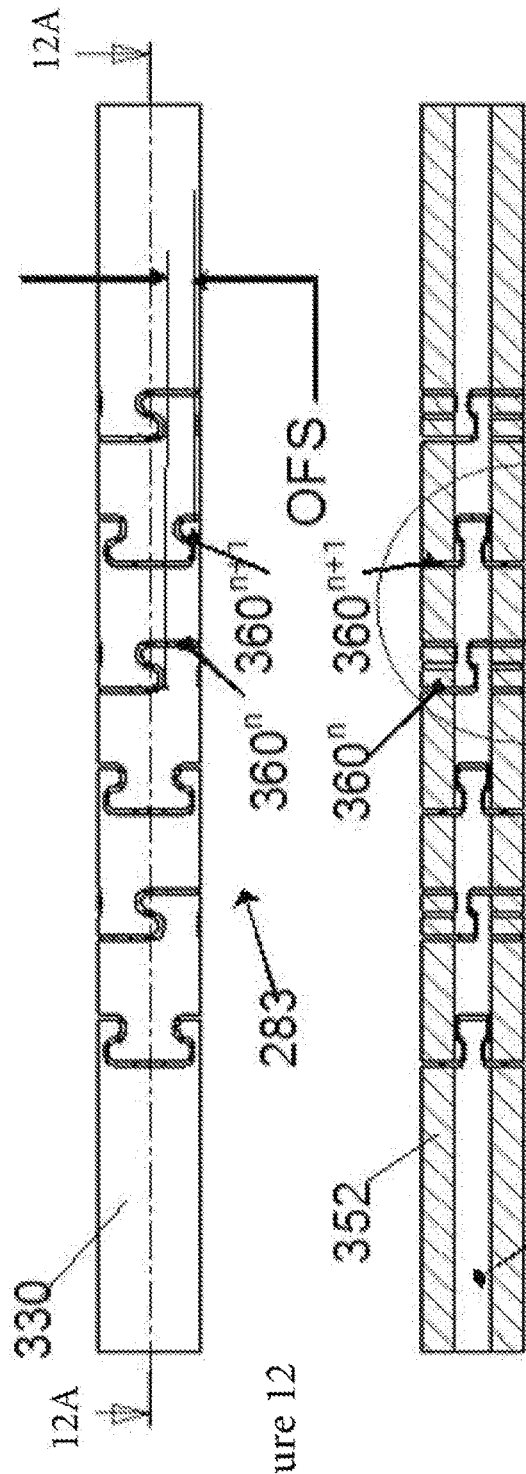
Figure 12
Figure 13A
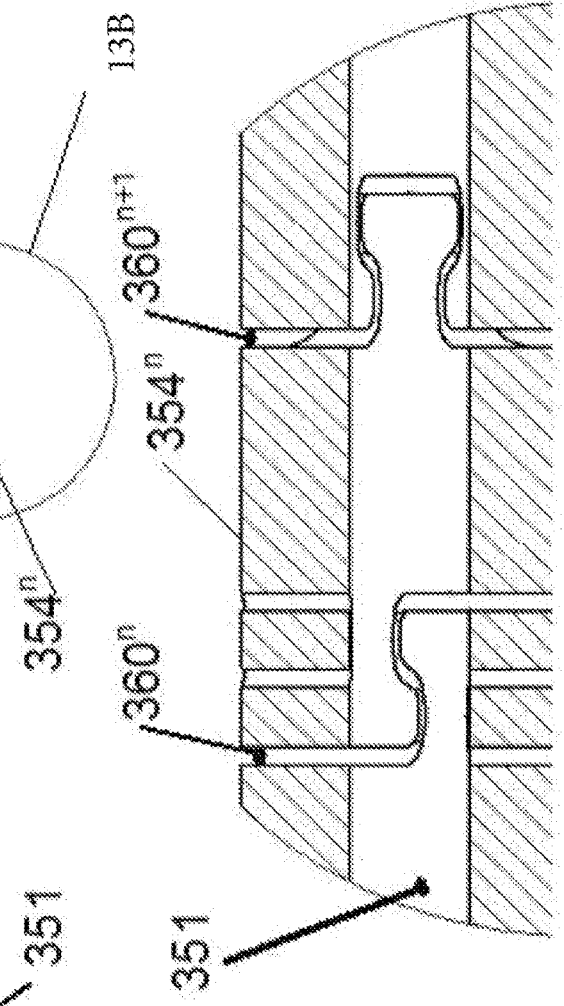
Figure 14

FLEXIBLE SHAFT FOR USE AS AN INTERNAL SPLINT FOR INDUSTRIAL APPLICATION

FIELD OF THE INVENTION

The present invention relates generally to the repair and connection of flexible tubing and semi-flexible structures using an internal flexible splint.

BACKGROUND OF THE INVENTION

The application of flexible fastening devices encompasses a broad spectrum of industries, included, but not limited to, manufacturing, construction, mining, transportation, agriculture, aviation, automotive, and medical. Flexible fastening devices, either tipped like screws or flat-end like bolts, have the characteristics in which the cylindrical portion of the device is bendable about the longitudinal length. Flexible fastening devices are useable in many applications, from manufacturing to medical, to secure to objects together.

In U.S. Pat. No. 3,627,354 a flexible connector is disclosed that comprises a tubular member having a central corrugated portion and having an uncorrugated end portion with braided strings to provide a mechanical friction connection. This, however provides a complicated and costly device.

The connection of two or more flexible structures or semi flexible structures is a challenge, especially when the entry points are not in alignment. This is exemplified in the connection of metallic, plastic, and rubber tubing, in addition to the repair of biological materials such as blood vessels and bones. Additionally, support of flexible structures in a flexed configuration can be difficult in that to maintain the curved configuration, the material must have more rigidity than would be advantageous in the remaining application.

The connection of two structures, such as tubing, is further complicated when the connecting device needs to accommodate fluid transfer. In such cases, the serpentine slot is filled with a polymer or the entire shaft is encapsulated in a polymer.

The present invention overcomes the deficiencies and problems evident in the prior art as described herein above by combining the following features into an integral, longitudinally, laterally and torsionally flexible segment of the component.

SUMMARY OF THE INVENTION

A flexible connecting rod, or internal splint, manufactured from a rigid material having a substantially cylindrical hollow body with a leading segment and a trailing segment, each having a securing area. The securing areas of the leading segment and trailing segment can be any from the group comprising securing slots, holes, threads, deployable fins, talons, expandable cages, and cement. At least one flexible center section formed by at least one slot following a sinuous, serpentine path to form a plurality of interlocking teeth to provide flexibility. The at least one slot can follow a helical path along a portion of the body, consist of multiple concentric slots, or be a combination of the two.

Each of the at least one slot has a proximal end and a distal end, with the proximal end being spaced from the trailing segment and the distal end being spaced from the leading segment. When multiple slots are used the proximal and distal ends of each slot can be spaced from one another or adjacent thereto. Each slot can have a varied flexibility and/or pattern in relationship to other slots, with increased or decreased flexibility with respect to other slots. The multiple slots can be separated by a non-slotted section.

Each of the slots can have sufficient width to form an unbound joint permitting limited movement in any direction upon application of tensile, compressive, and/or torsion forces. Each of the slots can also have an increased width in a first direction compared to a second direction to provide increased flexibility in the first direction.

The varied flexibility is achieved by varying the pitch of the helical slot and helix angle, with the helical angle being in the range of about 5 degrees to about 45 degrees, and/or the amplitude and frequency of the slot cycle. The varied flexibility can also be achieved by varying the width of the helical slot, instead of or in addition to the helical angle, amplitude, and frequency of the slot cycle. The slot width is between about 0.5% and about 15.0% of the diameter of flexible rod with a maximum of 20% to 25%.

The ratio of the amplitude of the path to the pitch of the slot is in the range from greater than 0.1 to about 0.8. The helical path of one or more slots is about 0.25 to about 5 cycles per diameter length and the helical angle ranges from about 5 degrees to about 20 degrees.

The flexible connecting rod can also comprise an elastomeric material interacting with the rod and selected from at least one of the group comprising: at least one of the at least one slot being filled; at least one portion of the inside core adjacent to the flexible center section being filled; said insider core being filled; extending through and filling the at least one slot; encompassing at least a portion of the exterior diameter of the rod; encompassing the exterior diameter, filling and extending through said at least one slot; encompassing at least a portion of said exterior diameter of the flexible connecting rod. The rigidity of the flexible connecting rod can be further varied through the use the elastomeric filler material having different stiffness properties, thereby enabling the use of thinner walls than would otherwise be required to produce equivalent rigidity. The use of an elastomer is disclosed in co-pending application Ser. Nos. 12/069,934 and 61/077,892 expired, and U.S. Pat. Nos. 6,053,922 and 6,447,518 the disclosures of which are incorporated herein as though recited in full.

The flexible connecting rod can further comprise a locking shaft having a flexible bar, multiple roller sets each comprising at least a pair of rollers and spacers, and an outer diameter dimensioned to be received in the flexible connecting rod. Either the spacers or rollers can be non-rotatably affixed to the bar while the other remains rotatable. The roller sets have a receiving hole offset from the center and dimensioned to receive said rod; and rotation of the bar rotates the multiple roller sets to wedge them against the interior of the flexible connecting rod.

The disclosed flexible connecting rod is manufactured from a rigid material appropriate for end use, and has a substantially cylindrical hollow body. The rod has a leading segment with an entry hole at a distal end and at least one securing means and a trailing segment having a trailing edge and an attachment mechanism. The body has at least one flexible center section, each having at least one slot to provide flexibility. In one embodiment the at least one slot follows a sinuous, serpentine path to form a plurality of interlocking teeth. The serpentine path can follow a helical path or a concentric path. The helical path of said at least one slot is about 0.25 to about 5 cycles per diameter length and the helical angle ranges from about 5 degrees to about 20 degrees The ratio of the amplitude of the path to the pitch of the slot is in the range from greater than 0.1 to about 0.8. The width of each slot between about 0.5% and about 5.0% of the diameter of said flexible rod. The at least one slot can alternatively follow a helical path. Each of the slots has a proximal end and a distal end, with the proximal end being spaced from the trailing segment and the distal end being spaced from the leading segment. When multiple slots are incorporated, the proximal end of a slot is spaced from a distal end of a subsequent slot. The first of the at least one flexible center section and a second of the at least one flexible center section can be separated by a non-slotted section.

Each of the at least one slot can have a varied flexibility in relationship to another of slot from the group comprising increased flexibility, decreased flexibility, equal flexibility. Each of the slots can have sufficient width to form an unbound joint permitting limited movement in any direction upon application of tensile, compressive, and/or torsion forces. Alternatively, each slot can have an increased width in a first direction compared to a second direction to provide increased flexibility in said first direction. The varied flexibility can be achieved by varying the pitch of the helical slot and helix angle, said helical angle being in the range of about 10 degrees to about 45 degrees. The flexibility can also be achieved by varying the width of the helical slot.

Advantageously, the slot is cut at an angle normal to the shaft using a computer controlled cutting technique such as laser cutting, water jet cutting, milling or other means. Additionally, this slot may be cut at an angle to the normal so as to provide an undercut slot; preferably the angle is in the range from about 5 to about 45 degrees from the normal.

The sinusoidal wave forms dovetail-like teeth, which have a narrow base region and an anterior region which is wider than the base region. Thus, adjacent teeth interlock. The teeth can have a configuration as illustrated in U.S. Pat. No. 4,328,839, the disclosure of which is incorporated herein by reference, as though recited in detail.

An important aspect of this invention therefore lies in providing a rod for insertion in, and connection of, nonlinear structures. An additional aspect is a mechanism that causes the flexible rod to become rigid to provide additional support to all or a portion of the structure being connected.

BRIEF DESCRIPTION OF THE DRAWINGS

Examples of the invention are illustrated in the drawings herewith. All of the figures are drawn on an undersized scale, and like structure in different figures bears like reference numerals.

FIG. 12 is a perspective view of the disclosed flexible connection rod with two circumferential slots spaced by an inflexible section in accordance with the present invention;

FIG. 13a is an illustration of variation of the change in orientation of the serpentine slot relative to the adjacent slot whereby the teeth of each adjacent circumferential slot is staggered or offset a variable distance;

FIG. 13b is a cross sectional view of the central segment through the longitudinal axis of FIG. 13a, showing the general pattern of the offset serpentine, circumferential slots along the length of the segment in accordance with the invention;

FIG. 14 is an exploded view of section 13B showing the gap and interlocking of the serpentine slot of two slots that have been offset or staggered, in accordance with the invention;

DESCRIPTION OF THE PREFERRED EMBODIMENTS

Figure 1:
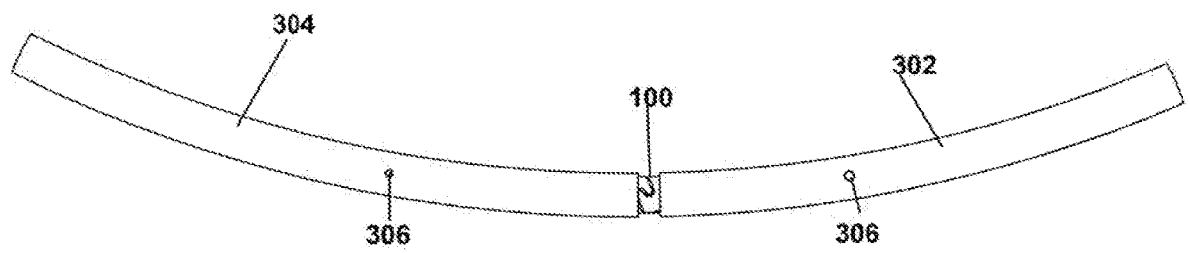
FIG. 1 illustrates the flexible connecting rod connecting two pieces of flexible tubing in accordance with the present invention.

For the purposes herein the term "flexible connecting rod", refers to a hollow, metal rod that connects two flexible or semi-flexible structures.

For the purposes herein the terms "slit" and "slot" are used interchangeably, consistent with their definitions, as follows:
 a. slot n. 1. A narrow opening; a groove or slit: a slot for coins in a vending machine; a mail slot.
 b. 2. A gap between a main and an auxiliary airfoil to provide space for airflow and facilitate the smooth passage of air over the wing.

For the purposes herein the term pitch as used herein is defined as:
 a. pitch—n.1. The distance traveled by a machine screw in one revolution.
 b. The distance between two corresponding points on adjacent screw threads or gear teeth. (American Heritage Dictionary, 3rd Edition, Copyright 1994)

For the purposes herein the term "cycle" shall refer to:
 a. Cycle—1. An interval of time during which a characteristic, often regularly repeated event or sequence of events occurs: Sunspots increase and decrease in intensity in an 11-year cycle.
 b. 2.a. A single complete execution of a periodically repeated phenomenon: A year constitutes a cycle of the seasons.
 c. 2b. A periodically repeated sequence of events: cycle includes two halves of the sine-wave like undulation of the slot path. (American Heritage Dictionary, 3rd Edition, Copyright 1994)

For the purposes herein the term "amplitude" shall refer to the maximum absolute value of the periodically varying quantity of the slot.

For the purposes herein the term "serpentine" shall refer to:
 a. 3 a: winding or turning one way and another <a serpentine road>
 b. b: having a compound curve whose central curve is convex. (Merriam-Webster online dictionary)

For the purposes herein the term "sinuous" shall refer to:
 a. a: of a serpentine or wavy form: winding,
 b. b: marked by strong lithe movements. (Merriam-Webster online dictionary)

For the purposes herein the term "serpentine" and "sinuous" are interchangeable and shall refer to a winding or turning one way and then another so as to not follow a straight line, except for brief instances.

For the purposes herein the terms "segment" and "section" are interchangeable and shall refer to slotted and unslotted area of the flexible rod, dimensioned to meet end use requirements.

For the purposes herein the term "helical", "helix" and "spiral" are interchangeable and shall refer to:
 a. 1 a: winding around a center or pole and gradually receding from or approaching it <the spiral curve of a watch spring> b: helical c: spiral-bound <a spiral notebook>
    2: of or relating to the advancement to higher levels through a series of cyclical movements. (Merriam-Webster online dictionary)

For the purposes herein the term "frequency" shall refer to the number of times a specified phenomenon occurs within a specified interval:
 a. Frequency.
 b. 1a. Number of repetitions of a complete sequence of values of a periodic function per unit variation of an independent variable.
 c. 1b. Number of complete cycles of a periodic process occurring per unit time.
 d. 1c.: Number of repetitions per unit time of a complete waveform, as of an electric current. The number of times the cycles form a repetitive pattern in one unit of length is the frequency of the slot pattern. The number of cycles "C" of the slot undulations superimposed upon the circumferential path which are present in one revolution around the shaft, is referred to as the cycles per revolution. (American Heritage Dictionary, 3rd Edition, Copyright 1994)

The terms antegrade and retrograde indicate the direction of introduction of the rod from proximal and distal portals, respectively.

While the present invention will be described more fully hereinafter with reference to the accompanying drawings, in which particular embodiments and methods of implantation are shown, it is to be understood at the outset that persons skilled in the art can modify the invention herein described while achieving the functions and results of this invention.

Flexible connecting fixation devices are useable in many applications from securing rubber seal strips, to connecting flexible fluid tubes to providing fracture fixation to a number of different bones. Accordingly, the descriptions that follow are to be understood as illustrative and exemplary of specific structures, aspects and features within the broad scope of the present invention and not as limiting of such broad scope.

The invention in one embodiment relates to a flexible rod having one or more flexible segments within a central section of the device. When containing multiple flexible segments, these segments can be separated by a solid section to position the flexibility of the structure. The flexible rod can also contain a segment, or segments, that also include threads or cross holes used for the placement of interlocking screws. The flexibility is created through the use of at least one sinuous helical slot formed in the center segment of the flexible connecting rod. In other embodiments, additional flexible segments also have at least one sinuous helical slot in either the same helical rotation and pattern or in an opposite rotation and/or different pattern. In another embodiment the flexible section or sections has a flexible segment that has at least one helical, sinuous slot within a section of the element that is embedded within a polymer or other flexible material so as to fill the slot with the flexible material as disclosed in U.S. Pat. Nos. 6,053,922 and 6,447,518 which are incorporated herein as though recited in full. In an additional embodiment the flexible rod uses a hollow flexible element that encompasses a polymer or other flexible material within its central core without extending into the sinuous slot(s). A further embodiment uses a flexible slotted segment within the element that contains a polymer or other flexible material within the central core with the flexible material extending radially outward through the sinuous slot(s). The flexible rod can further incorporate a flexible slotted segment that contains a polymer or other flexible material within the central core of the flexible segment that extends radially outward through the slot and encompasses the outer surface of the element and/or the flexible segment.

In applications where the disclosed flexible connecting rod is used to connect flexible or semi-flexible structures and additional stability is required after implantation of flexible connecting rod, the appropriate cement or other materials can be injected in the entry holes. The slotted flexible section of the rod provides a flow-through mechanism for cement that is used for production of a cement jacket around the rod, such that rod will be anchored in a highly stable manner after being implanted. This is especially advantageous when the flexible connecting rod is being used as a replacement for a dowel.

The disclosed flexible rod can also be used to provide support in critical areas as well as, when combined with the disclosed locking shaft, to maintain a flexible structure in a user determined curve.

In addition to connecting two flexible structures, the disclosed flexible connecting rod can be used to connect two structures that are in nonlinear alignment. This use can be applicable to furniture or bones and would incorporate a smaller flexible section with longer inflexible proximal and distal ends.

FIG. 1 is a diagrammatic illustration of the connecting rod 100 positioned into two flexible structures, in this illustration tubing 302 and 304, where each end is accessible for securing with a securing member 306, such as a pin. The nature of the securing member 306 will be dependent upon the material being connected and will be known to those skilled in the art.

Figure 2:
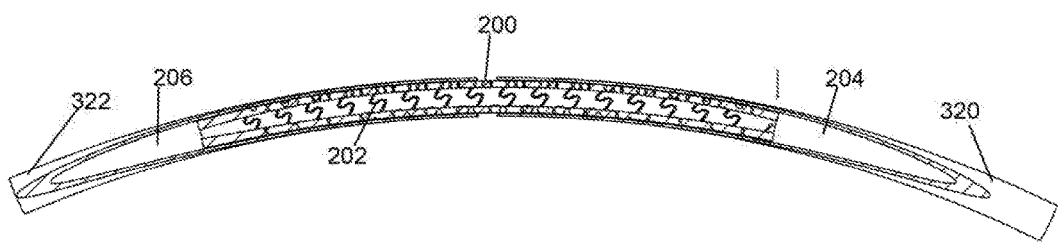
FIG. 2 is a cutaway of a flexible connecting rod in accordance with the present invention.
Figure 3:
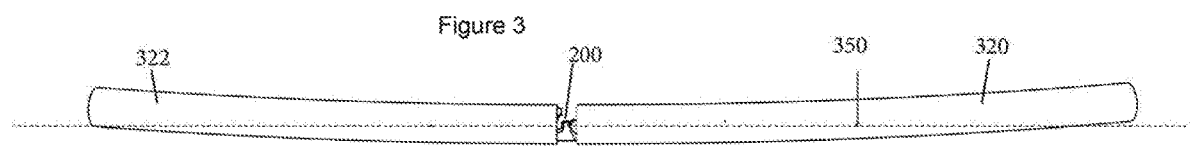
FIG. 3 is a view of a slightly flexed flexible rod within the flexible tubing of FIG. 2 in accordance with the present invention.

The flexible connecting rod 200 illustrated in FIG. 2 is an example of a flexible connecting rod, using a single slot 202 in the helical path illustrated above, having a closed distal end 206 and proximal end 204. To facilitate insertion into the tubes 322 and 320, each of the proximal end 204 and distal end 206 come to a point. This design would be advantageous for use with applications that do not require fluid flow and can be secured with an adhesive. In FIG. 3 the flexible connecting rod 200 is shown inserted in the flexible tubes 320 and 322 and slightly flexed from the normal plane indicated by line 350.

Figure 4:
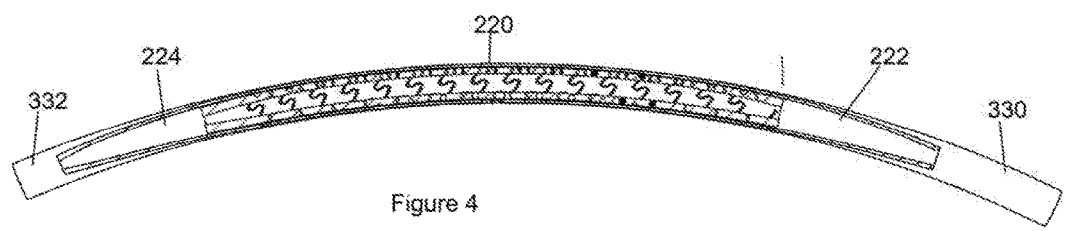
FIG. 4 is a cutaway of a flexible connecting rod allowing fluid flow in accordance with the present invention.

In applications where fluid transfer within the flexible structure being connected is of concern, the embodiment of FIG. 4 is incorporated. The flexible connecting rod 220 has an open distal end 224 and open proximal end 222 to enable fluid to flow through the flexible tubing 330 and 332. To prevent fluid leakage the flexible tubing 330 and 332 should abut one another and the securing member maintained in place with an adhesive. An elastomeric coating, as disclosed hereinafter, can also be applied to prevent fluid leakage. In this embodiment the distal end 224 and proximal end 222 have a reduced diameter to permit easier insertion into the tube 322. The need for diameter reduction as well as the degree of reduction will depend upon end use and will be evident to those skilled in the art.

Figure 5:
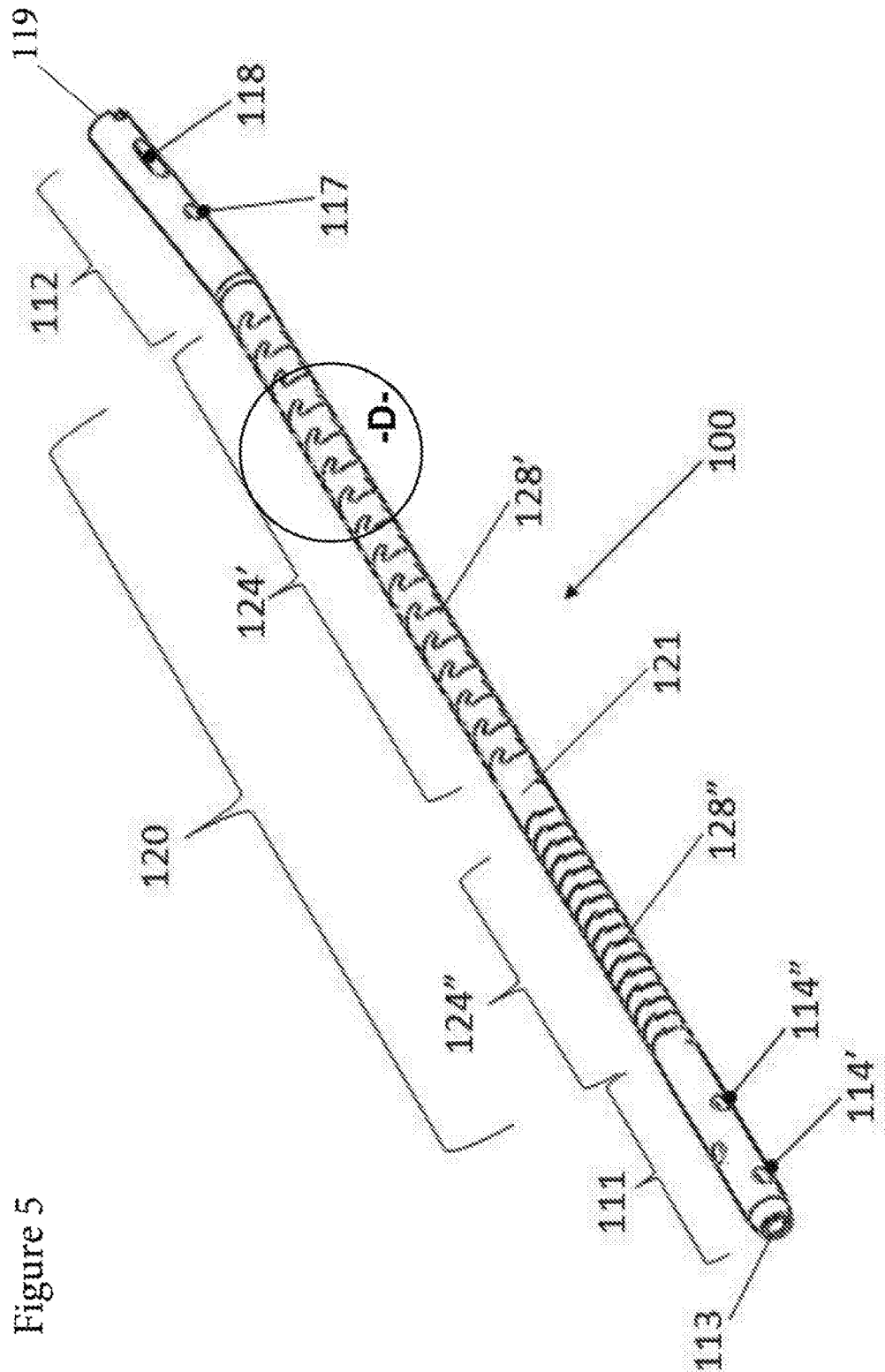
FIG. 5 is a plan view of the disclosed flexible connecting rod in accordance with the present invention.

In FIG. 5, the described flexible connecting rod 100 comprises leading end segment 111 and a trailing end segment 112 axially spaced apart by a substantially cylindrical, flexible center segment 120. The leading end segment 111 is furnished with an entry hole 113 to the central core 115 of the rod 100 and one or more transverse locking holes 114', 114". The trailing end segment 112 has a trailing edge 119 with an attachment mechanism 109 and transverse slot 118 and/or transverse locking hole 117. The center section 120 in this embodiment has two flexible sections, although one or more can be used and dimensioned accordingly, proximal flexible section 124', and distal flexible section 124" in which a serpentine, spiral slot 128', 128", respectively is superimposed on a helical path about the shaft 121 of the center section 120. The flexible section 124" extends, in this embodiment, generally from the proximal end of the leading end segment 111 about one third the length of the rod 100. Spaced slightly from the proximal end of the distal flexible section 124" is the proximal flexible section 124' that extends to the distal end of the trailing segment 112. Through the rod 100 is a hollow cavity 115 extending from the leading edge 113 to the trailing edge 119. The leading edge 113 in this figure is slightly beveled, however whether there is a bevel and the degree to which there is a bevel, will vary depending upon end use. The flexible connecting rod illustrated in FIG. 5 is applicable for uses where each end in the structure is accessible to enable securing members to be inserted.

Figure 6:
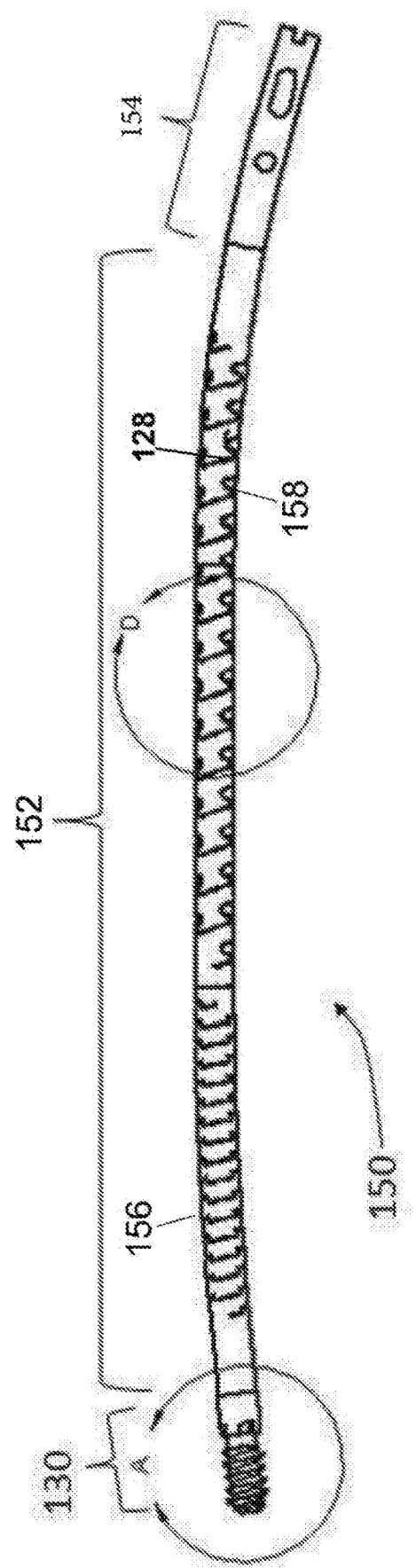
FIG. 6 is a plan view of the flexible connecting rod with a threaded end for distal end attachment and showing area for detail of the sinuous slot in accordance with the present invention.

In FIG. 6 the flexible connecting rod 150 has a threaded leading end segment 130 for securing the rod 150 to the structure. In this embodiment the threaded leading end segment 130 is used when the distal portion of the flexible connecting rod 150 cannot be accessed for insertion of a pin or other securing device. Other means, applicable to the structure, of securing the leading and trailing ends to the structure can be employed. Such means include, but are not limited to, deployable fins, talons, expandable cages, and the use of deployable cement. The flexible section, 152, as with the embodiment illustrated in FIG. 5, contains a distal flexible section 156 and a proximal section 158 having differently dimensioned serpentine patterns with the trailing end 154 configured to receive a locking member.

Figure 7:
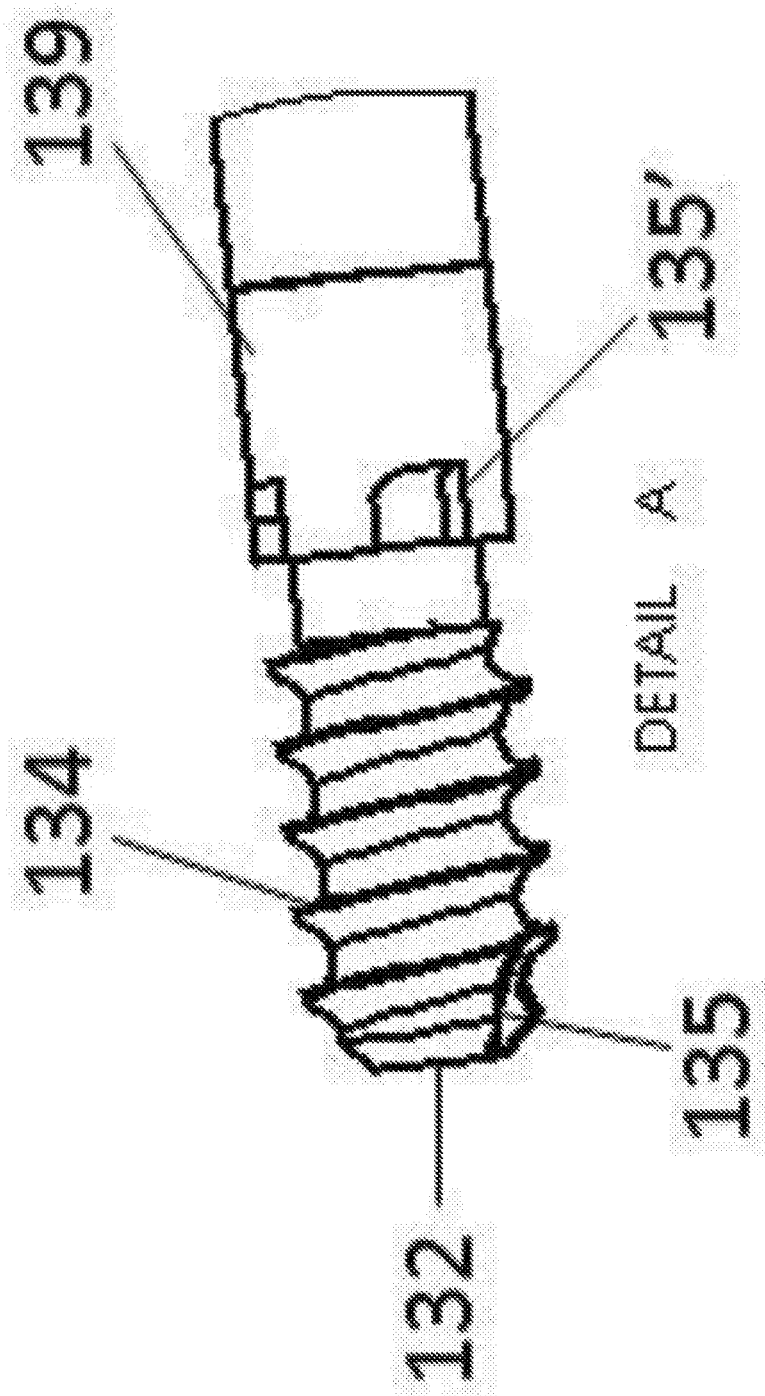
FIG. 7 is a detailed view of the threaded leading segment of FIG. 6 in accordance with the present invention.
Figure 8:
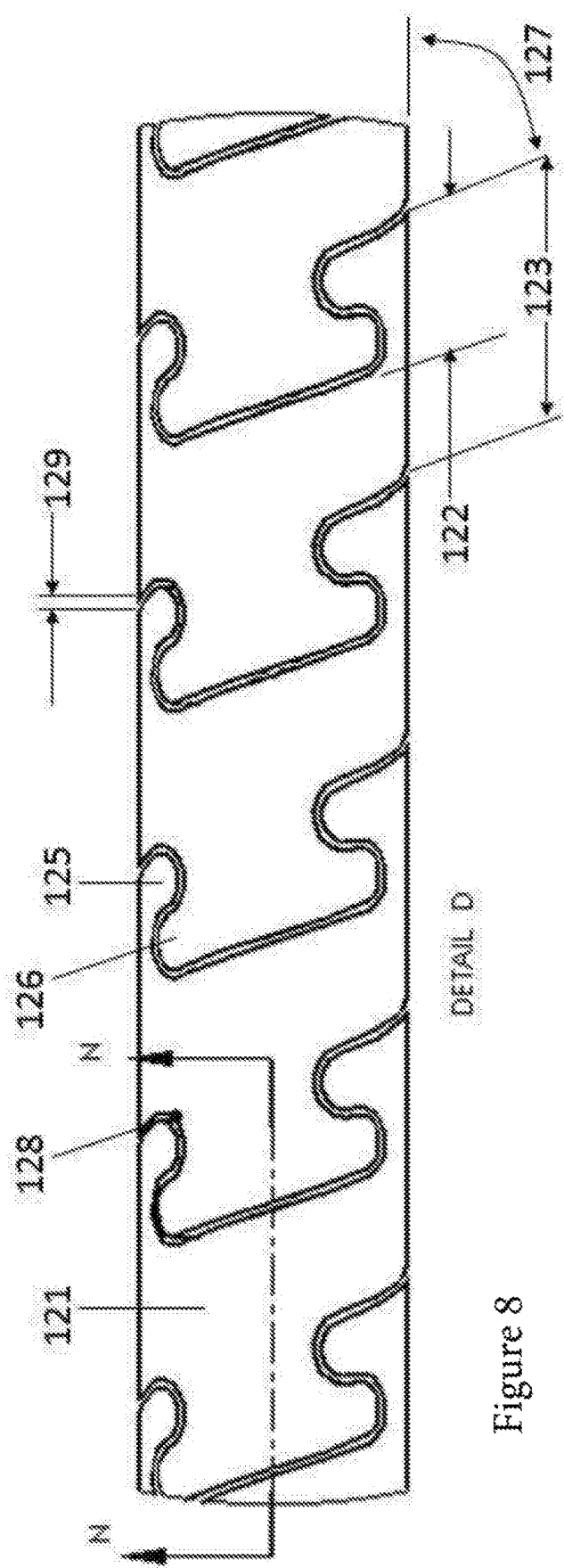
FIG. 8 is a detailed view of the slot comprising the flexible segments of the flexible connecting rod in accordance with the invention.
Figure 8A:
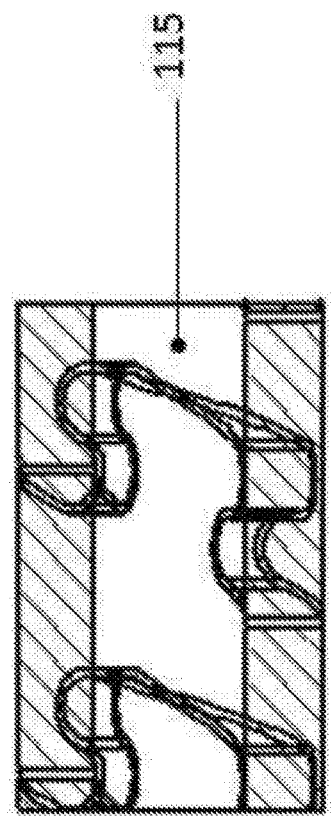
FIG. 8a is a detailed perspective of the serpentine slot cut in accordance with the present invention.

FIG. 7 illustrates the threaded leading end segment 130 of the flexible rod 150 of FIG. 6 in which a leading threaded end segment 130, is furnished with a shank 139 for attachment with the rod 100, an end 132, screw thread 134 and a threaded cutting recess 135 at the end 132 and cutting recess 135' on the shank 139. Depending upon the application, the cutting recess 135' can be eliminated, leaving the screw thread 134. This design is advantageous for connecting a solid, or semi-solid, structure to a flexible structure where the screw head embeds the connecting rod into the solid, or semi-solid structure. Due to the threaded leading end segment 130, fluid transfer is restricted to the spiral slots and is not optimal for high fluid flow applications, FIG. 8 and FIG. 8a are exploded views of section D in FIGS. 5 and 6, as well as being representative of the serpentine slots used herein, showing the serpentine slot 128 within the shaft 121' of the flexible section 124' of rod 100. The slot 128, having a width 129, is cut with a general helix angle 127 of about 10 to 80 degrees with respect to the longitudinal axis of the section 124". In this embodiment the slot 128 is cut in a serpentine pattern having an amplitude 122 and interlocking teeth 126, 125 with a pitch 123. It should be noted that the serpentine slot 128 can be used on all embodiments herein. Although length and width can vary dependent upon end use, the basic concepts as illustrated in this embodiment are consistent. The slot 128 is representative of all the slots disclosed herein in that way that it is cut through the shaft 121 into the core 115. Although the slots disclosed herein are of different patterns, this is purely a function of flexibility and all have the same basic construction. In the following description of the criteria of the slots, no reference numbers specific to other figures are used, as the criteria are applicable to all slot configurations.

In industrial applications, the slot width would be between about 0.5% and about 15.0% of the diameter of the connecting rod, with a maximum of about 20% to 25%. For a given diameter, the higher the percentage slot width, the flexible the shaft will be more flexible.

In applications where smaller dimensions are required, such as medical, the helical path of the slot 128 is about 0.25 to about 5 cycles per diameter length. In order to provide the desired flexibility, while maintaining support, the width of the slot 128 should not exceed about 0.075 of an inch in a rod or shaft having a diameter in the range from about 0.10 to about 0.750 inches, with a general width of about 0.005 to about 0.025 inches. Alternatively, the width to diameter percentages can be between about 0.5% and about 5.0% of the diameter of the element. The helical angle ranges from about 5 degrees to about 20 degrees.

Figure 10:
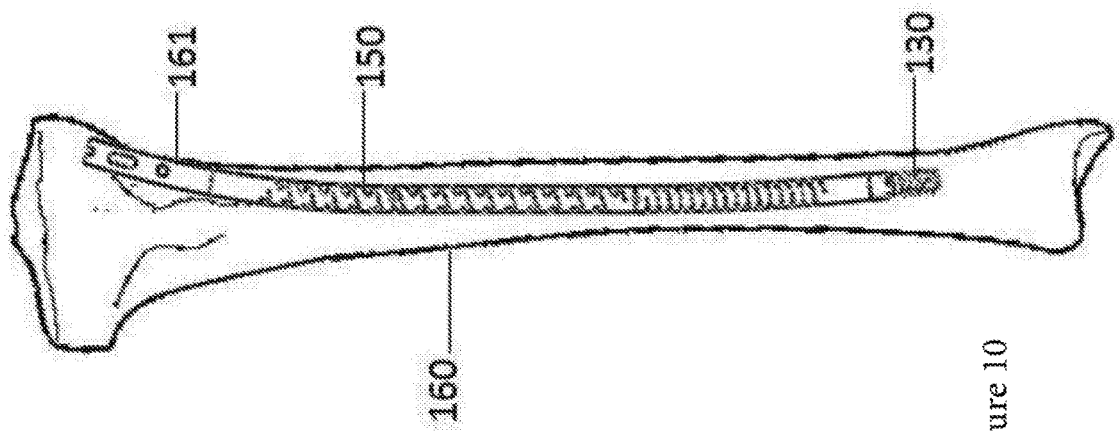
FIG. 10 is a cutaway view of the flexible intramedullary rod fully implanted into the tibia In accordance with the invention.
Figure 9:
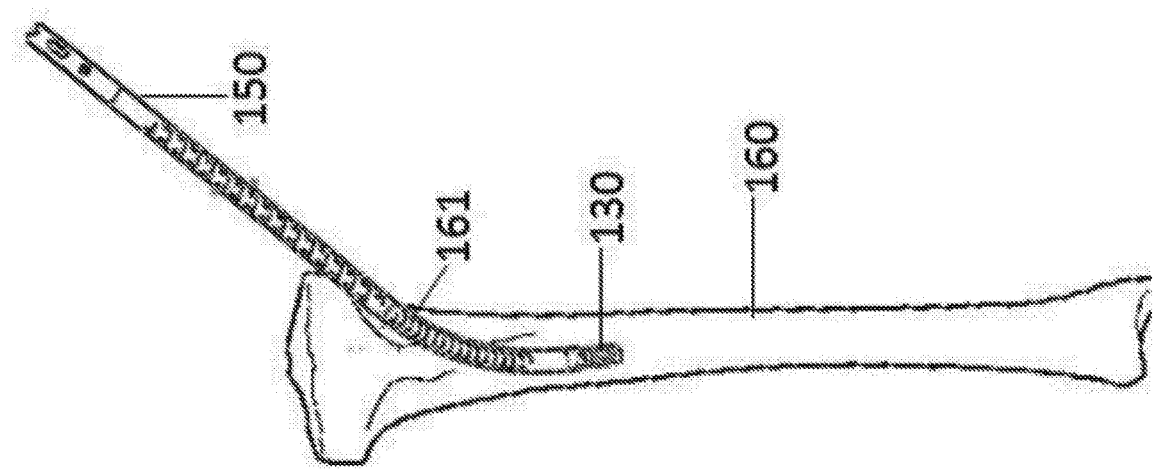
FIG. 9 is a cutaway view of the flexible intramedullary rod being inserted in the tibia showing its flexibility to provide for lateral entry into the tibia in accordance with the present invention.
Figure 11:
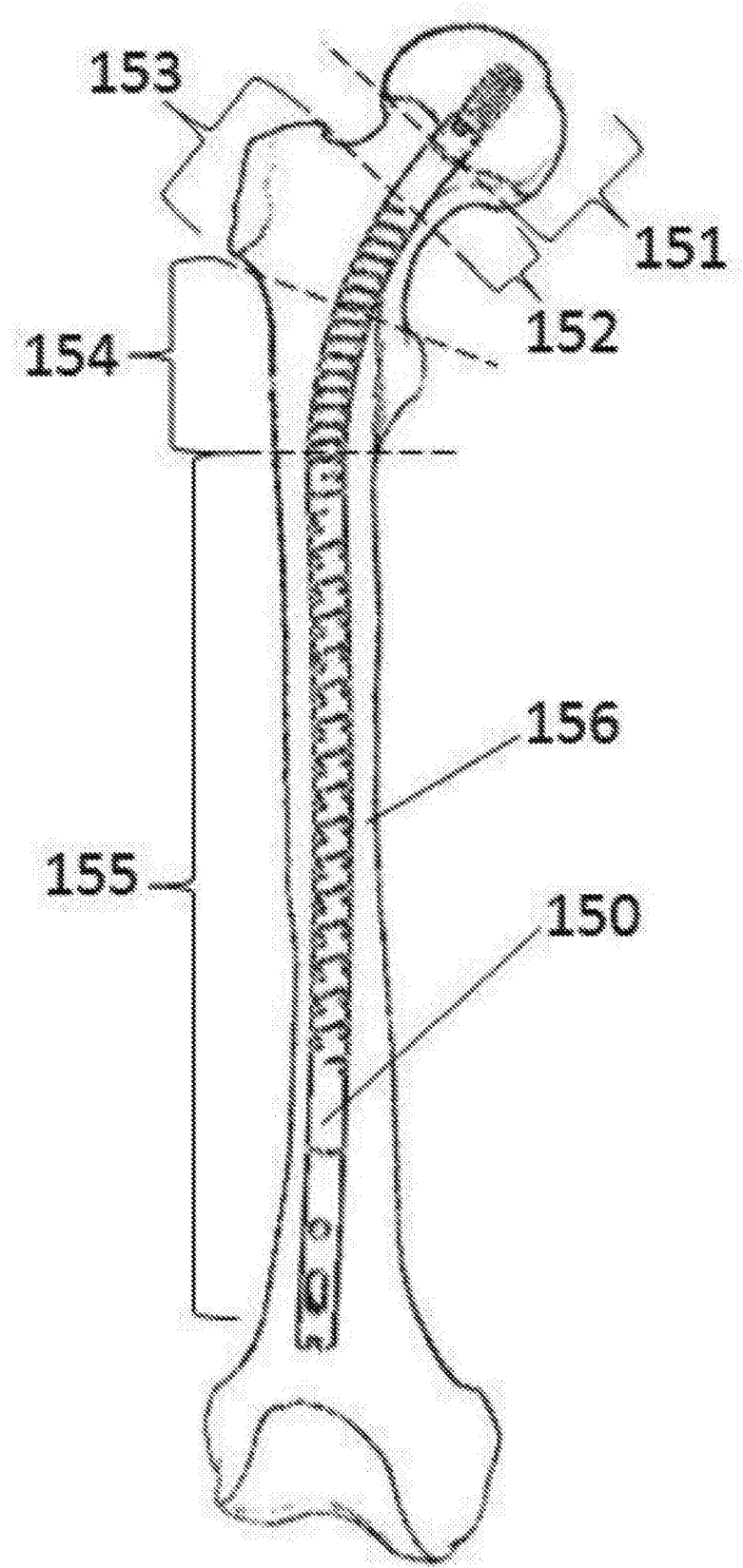
FIG. 11 is a cutaway view of a femur having the flexible intramedullary rod implanted in a retrograde fashion in accordance with the present invention.

One of the uses for the disclosed flexible connecting rod is in medical for the repair of bones. An example of medical uses are illustrated in FIGS. 9-11. FIG. 9 is a diagrammatic illustration of the connecting rod 150 being positioned retrograde in a tibia 160 at an entry point 161 on the medial aspect of the tibia with the leading thread end segment 130 positioned in the tibia below the point of entry 161.

FIG. 10 is a diagrammatic illustration of the connecting rod 150 fully positioned retrograde in a tibia 160 from the entry point 161 on the medial aspect of the tibia with the leading thread end segment 130 positioned in the tibia.

FIG. 11 is a diagrammatic illustration of an additional embodiment of the intramedullary rod 150 positioned retrograde in a femur 156 with the leading thread end segment 130 positioned in the femoral head 151 as would be used for a fracture of the femoral neck 152, the intertrochanteric 153, the subtrochanteric 154 or mid shaft 155 region.

In FIG. 12 the flexible connecting rod 250 contains two flexible areas 254 and 260 separated by an inflexible section 256. As with the prior designs, a proximal end 262 and distal end 264 are used to secure the connecting rod 250 within the structure.

In the embodiment illustrated in FIGS. 13a, 13b, and 14, the serpentine pattern of slot $360^{n+1}$ is offset or staggered a rotational distance OFS from the adjacent slot $360^n$ By staggering the serpentine pattern as illustrated, the bending characteristics, i.e. the bending strength and flexibility, can be changed to provide differences or uniformity with respect to the rotational axis.

The sectional view 12A of central segment 283 of FIG. 13a is shown in FIG. 13b. A magnified view 13B of the slot $360^n$ is illustrated in FIG. 14. The slot $360^n$ representative of all the slots disclosed herein in the way that it is cut through the wall 352 into the core 351.

Although the slots disclosed herein are of different patterns, this is purely a function of flexibility and all have the same basic construction. The criticality to the disclosed invention lies in the ratios and dimensions rather than the process of placing a rod or tube. The disclosed descriptions of the criteria of the slots, are applicable to all slot configurations. It should be noted that the number of slots, width or each slot, whether they are helical or concentric, the same or different patterns within a rod, etc. can vary to achieve the desired flexibility.

Figure 15:
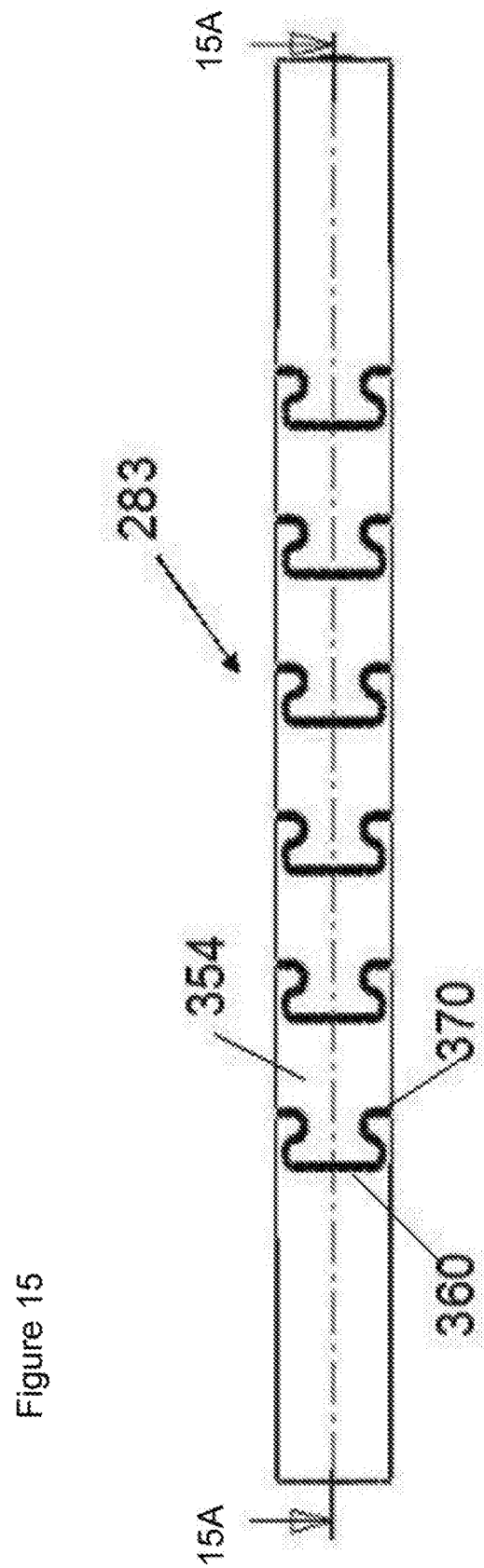
FIG. 15 is a schematic representation of the central segment of FIG. 12, showing general pattern of the circumferential serpentine slots with an elastomer filler material in the slot in accordance with the invention.
Figure 16:
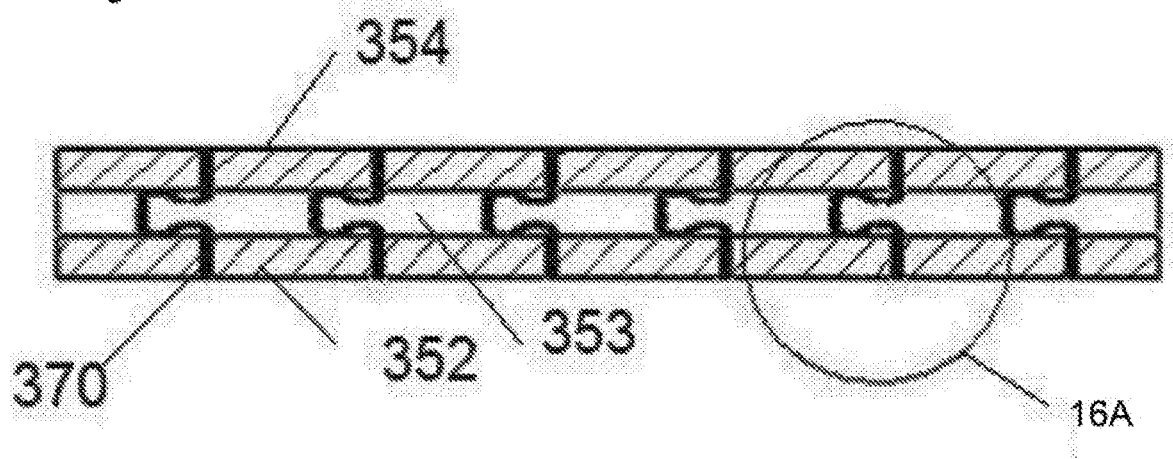
FIG. 16 is a sectional illustration though the longitudinal axis 15A-15A shown in FIG. 15 of the central segment showing the slot with a resilient filler in a portion of the slot in accordance with the invention.
Figure 17:
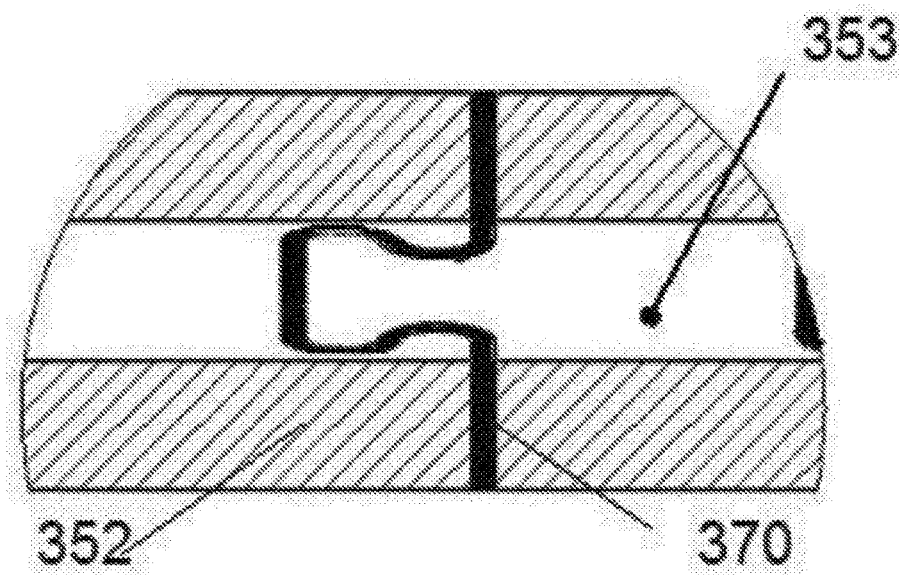
FIG. 17 is a magnified view of the area 16A in FIG. 16 in accordance with the invention.

In the embodiment illustrated in FIGS. 15, 16 and 17, an elastomeric polymer, or other flexible material, 370 fills only the slot 360 of the central segment. The exterior surface 354 of the central segment remains uncovered by the material 370 as does the interior surface 353. The addition of the elastomeric material 370 to the slot 360 provides resistance to the flexibility of the segment 283 as well as preventing ingress or egress of internal or external material into the slot. It should also be noted that whether the elastomeric material fills all slots in the rod will depend upon end use. The placement of filled and unfilled slots affecting the flexibility however will also permit fluid flow.

Figure 18:
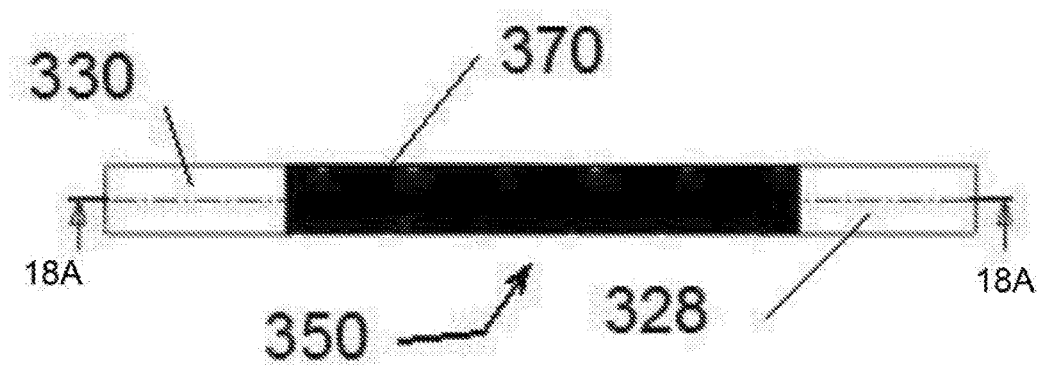
FIG. 18 is an exterior view of the central segment with the center portion encapsulated with a resilient filler in accordance with the invention.
Figure 19:
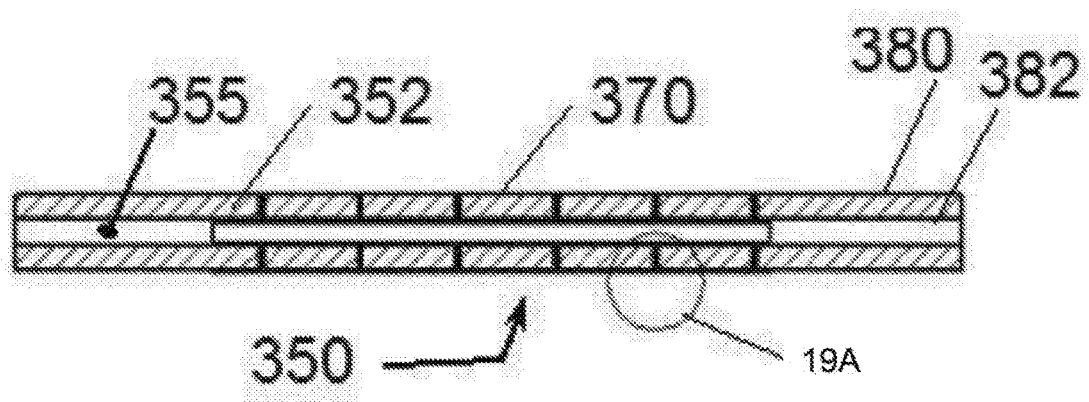
FIG. 19 is a sectional illustration though the longitudinal axis 18A of the central segment in FIG. 18 showing the filled slot with a resilient filler encapsulating the entire segment but not filling the central core.
Figure 20:
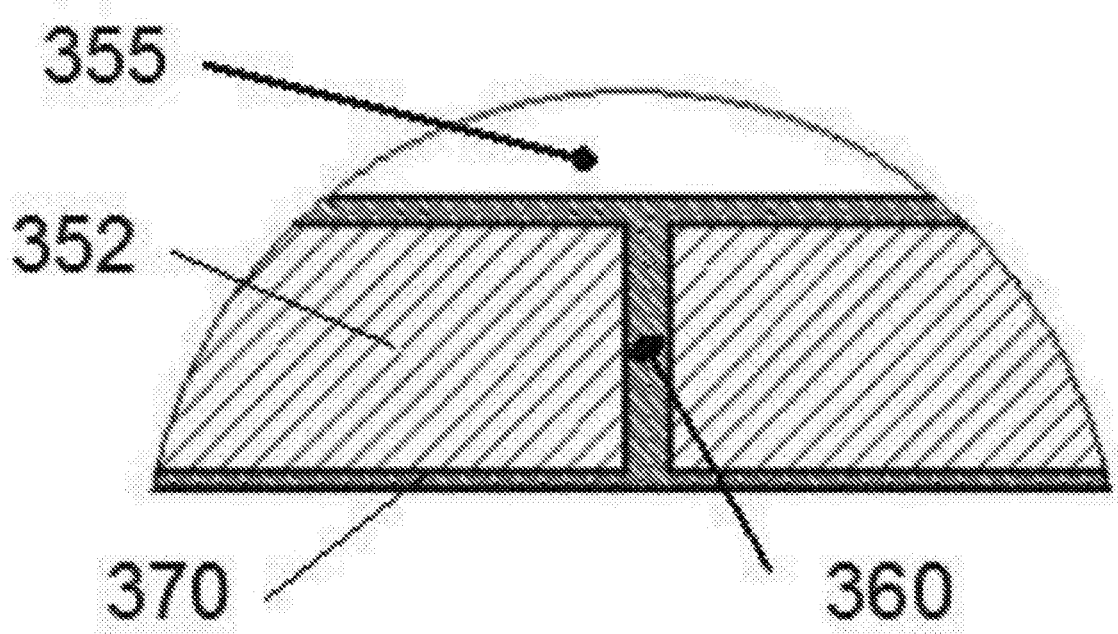
FIG. 20 is a magnified view of the area 19A in FIG. 19 in accordance with the invention.

In FIGS. 18-20 the elastomeric material 370 encapsulates the central segment 283 as well as filling the slots 360. In this embodiment, the interior surface 430 and exterior surface 328 are covered with the elastomeric material 370 and the slots 360 are filled to prevent tissue ingrowth into the slots 360 and increase the stiffness of the rod. The core 355, of the encapsulated segment 350, however, remains hollow as seen in section 30A-30A in FIG. 31. Although in these figures the elastomeric material 370 also fills the slots 360 passing through wall 352 as shown in FIG. 32 of the enlarged section 31A, it should be noted that the elastomeric material 370 can alternatively only encapsulate the segment without filling the slots 360. Additionally, just the interior or exterior of the segment can be covered with the elastomeric material with the slots being either filled or unfilled. The encapsulation can be only at the portion of the rod that is flexible or can extend the entire length of the rod. As noted above, the addition of the elastomeric material 370 increases the resistance to flexing and is not reflective of the advantages of encapsulating segment 350 with the elastomeric material 370.

Figure 21A:
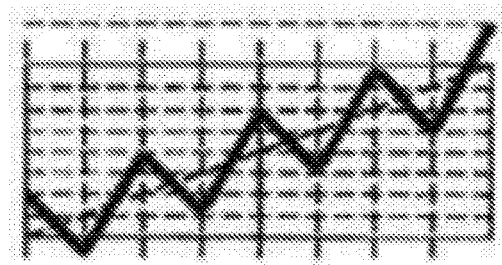
FIGS. 21a-k shows possible variations of the serpentine slot in accordance with the invention.
Figure 21B:
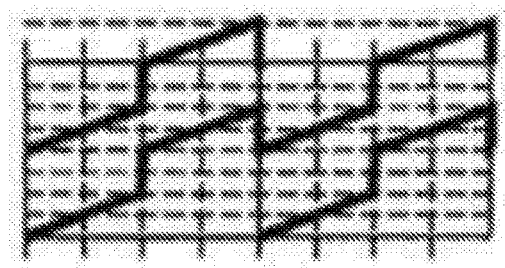
Figure 21C:
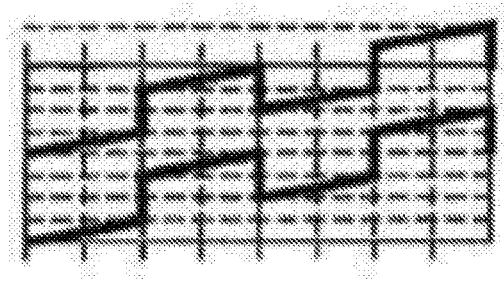
Figure 21D:
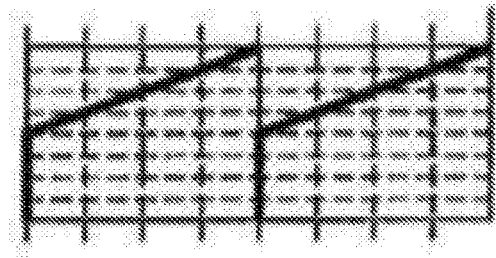
Figure 21E:
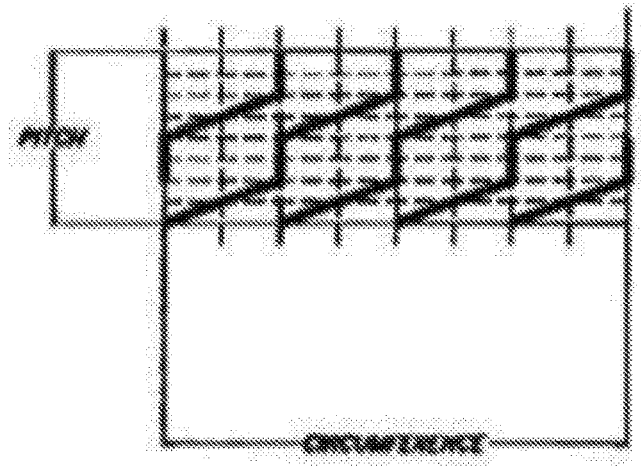
Figure 21F:
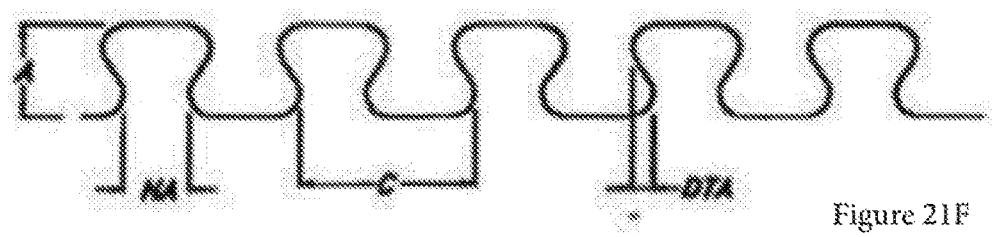
Figure 21G:
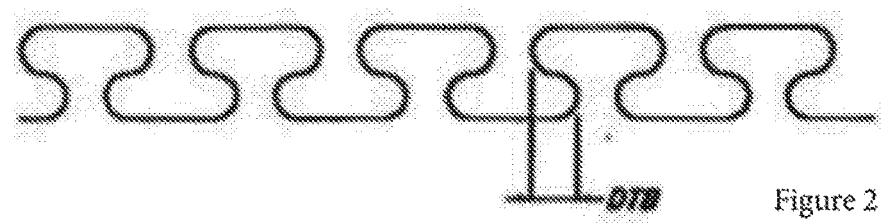
Figure 21H:
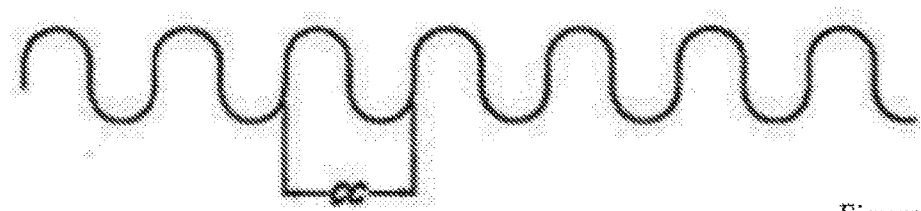
Figure 21I:
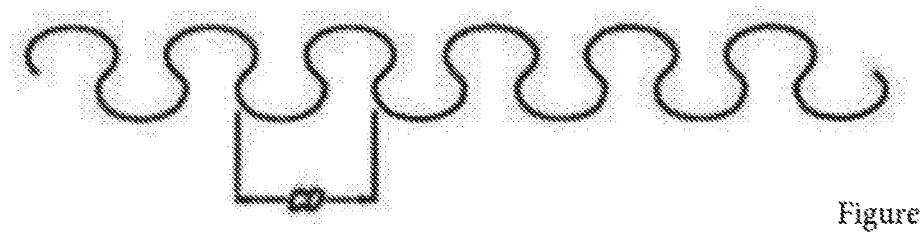
Figure 21J:
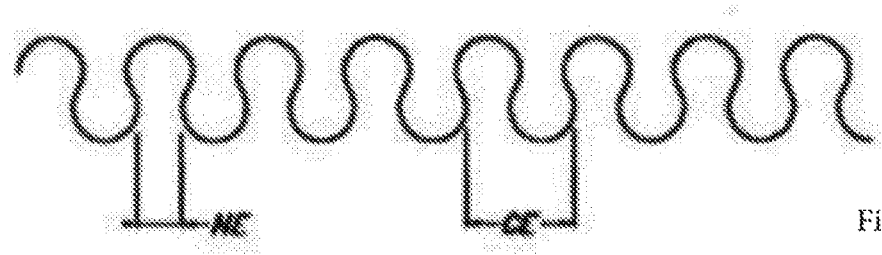
Figure 21K:
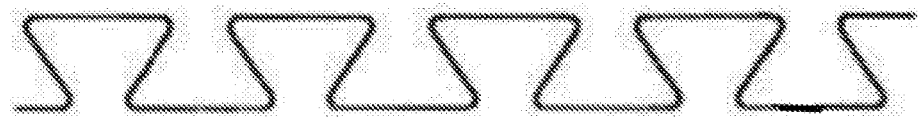

A variety of slot patterns are illustrated in FIG. 21A-K. The patterns are representative of patterns that can be used and are not intended to be all inclusive. As illustrated in FIG. 21A, and indicative of all patterns, the pattern has a cycle length C, which includes a neck region NA. The wider the neck region the greater the strength of the connector, that is, the greater the torsional forces which the flexible shaft can transmit. The ability of the device to interlock is dependent in part upon the amount of overlap or dovetailing, indicated as DTA for FIG. 9A and DTB for FIG. 21B. The patterns illustrated in FIGS. 21C and 21G-21K do not provide dovetailing, and require a helix angle that is relatively small. Pattern 9F is another interlocking dovetail pattern that can be used with a larger helical angle than non-dovetailing patterns The patterns of FIGS. 21H-21K is an interrupted spiral in which the slot follows the helical path, deviates from the original angle for a given distance, and then resumes the original or another helix angle. Patterns, as shown in FIGS. 21D, 21E, 21F, 21H through 21K can have a configuration as illustrated in U.S. Pat. No. 6,447,518, the disclosure of which is incorporated herein by reference, as though recited in detail.

Any of the segments of the flexible rod can be either non-flexible or can be made flexible by the incorporation of a slot with a serpentine path along a helical or concentric path, or combination thereof, within the segment.

Figure 22:
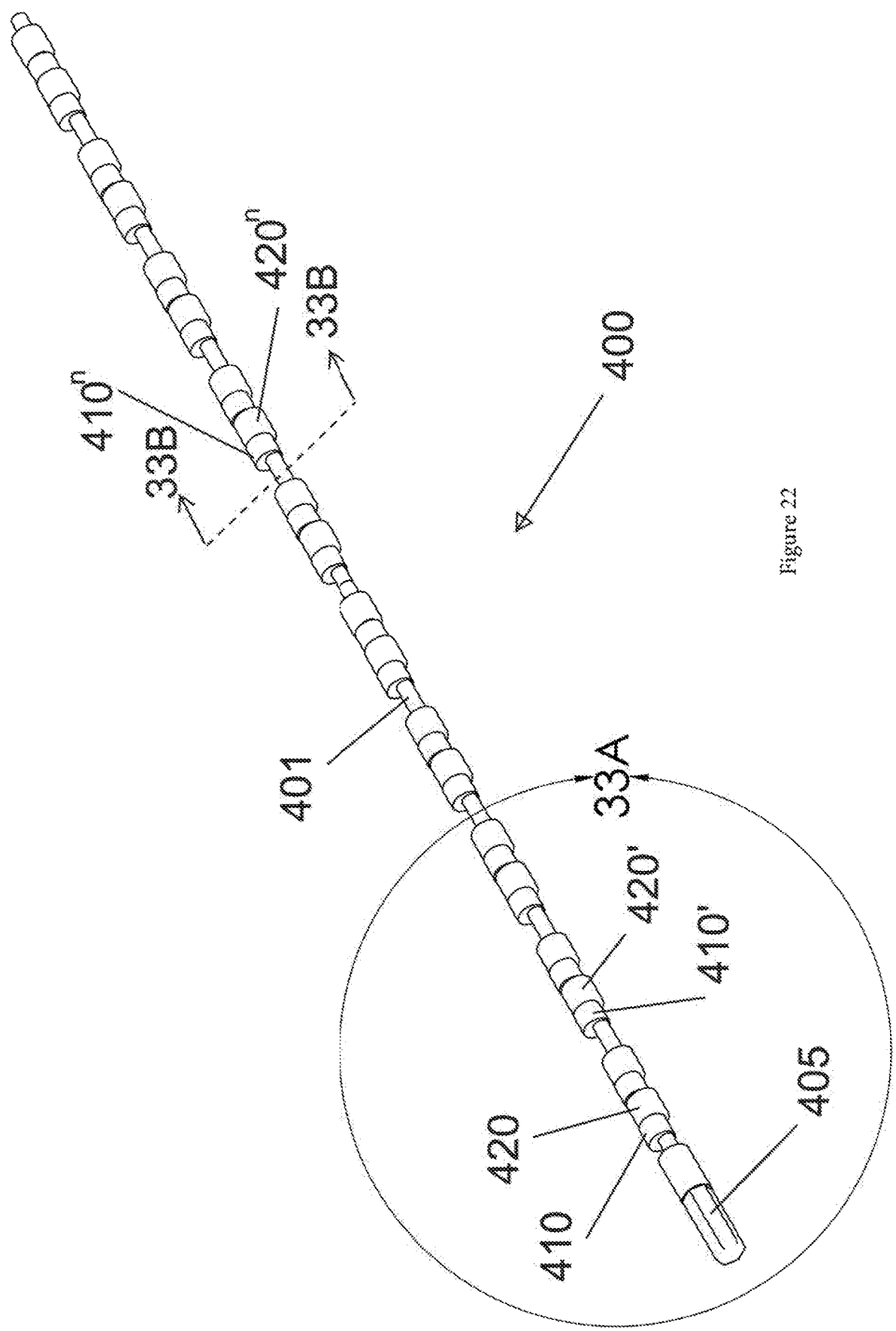
FIG. 22 is a perspective view of a locking shaft that, when inserted in the central cavity of the rod locks the rod in position (curvature) in accordance with the invention.
Figure 23:
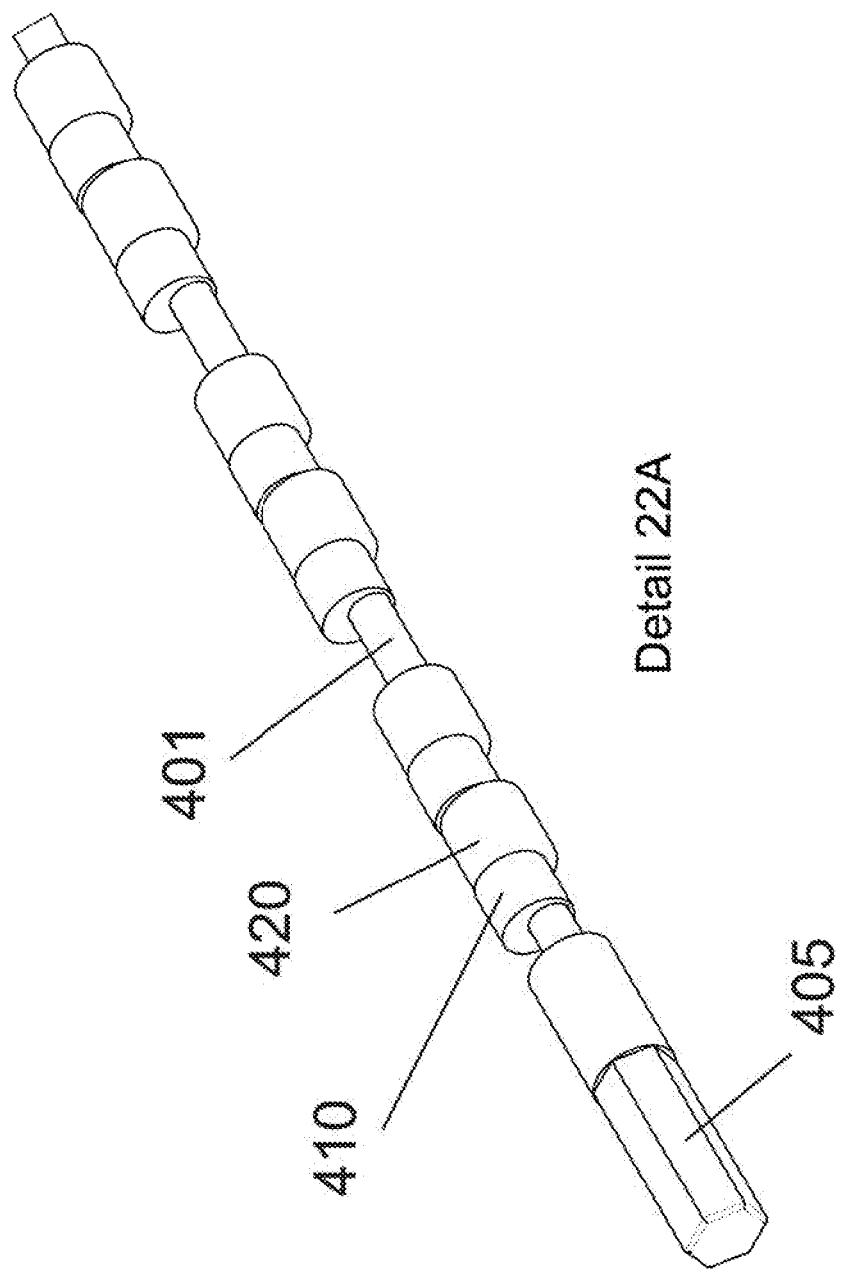
FIG. 23 is a plan view of the proximal end of the locking shaft of FIG. 22 in accordance with the invention.

The disclosed flexible connecting rod can also be used as a structural support to maintain flexible structures in a user determined curved position. In this application, illustrated in FIG. 22, a rod or similar type device can be inserted in the central core 115 to lock the curvature the flexible connecting rod 100 in a user determined shape. This can be advantageous whether maintaining tubing around a solid object or matching the natural curvature of the bone. One such locking shaft 400 is illustrated in FIGS. 22 and 23 which is comprised of sets of spacers 420 and movable rollers 410. Sets of these spacers $420^n$ and rollers $410^n$ are positioned along a rod 401 at multiple intervals, determined at time of manufacture. In most embodiments the spacers $420^n$ are fixed to the rod 401 while the rollers $410^n$ are free to rotate about the rod 401, although both spacers 420 and rollers 410 can rotate. The number and size of the sets, as well as the spacing in between is depend on end use and will be obvious to those skilled in the arts. At the driving end, or trailing section, of the locking shaft 400 is an attachment end 405 that is used to insert the locking device 400 and rotate the locking device 400 when required. A locking bolt can also be used to secure the locking shaft 400 to the flexible rod 100.

Figure 24:
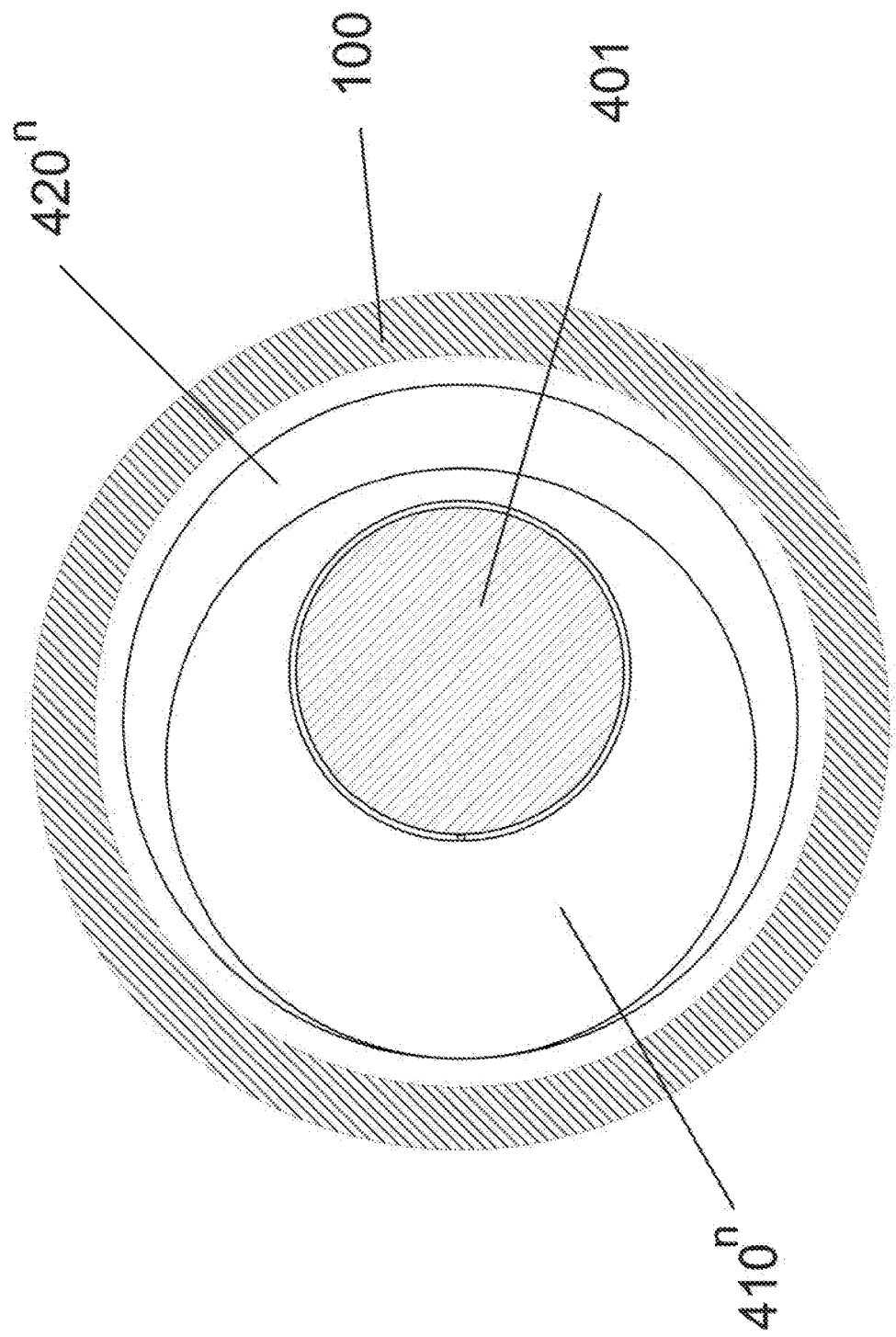
FIG. 24, is a front view of the cam and spacer in line as they would be when the locking shaft is inserted into the rod in accordance with the invention.
Figure 25:
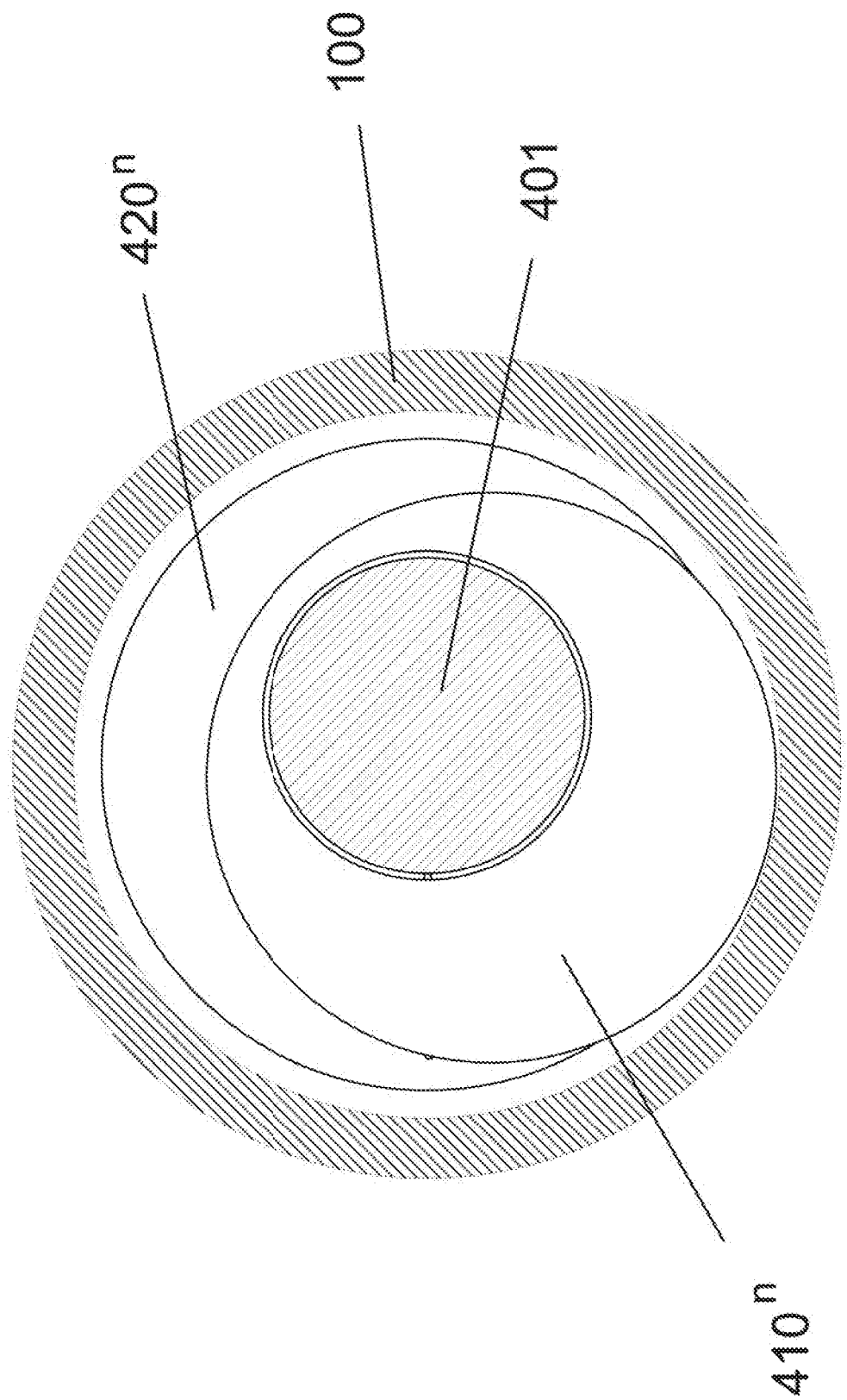
FIG. 25 is a front view of show the segment of the cam mechanism after the locking shaft has been inserted and locked in place in accordance with the invention.

In at least the spacer 420, and in some embodiments both spacer 420 and roller 410, the receiving hole for the rod 401 is offset from its center. This locks, upon rotation, the spacers 420 against the interior wall of the rod 100 creating the desired rigidity. The dimensioning between the outer diameter of the spacers 420 and rollers 410 and the inner diameter of the rod 100 must be such as to prevent the spacers 420 and rollers 410 from freely rotating within the interior of the rod 100. FIG. 24 shows the relative orientation of the spacer 420″ and roller 410″ when initially inserted into the central core of the flexible rod 100. FIG. 25 shows the relative orientation of the spacer 420″ and roller 420″ after the rod 401 has been rotated after insertion. When rotated, the rollers 410″ act as a wedge to push the spacers 420 up against the opposite wall thus locking the two in the interior diameter of the rod 100. With the multiple spacers 420 all locking within the interior of the rod 100, the rod 100 will become rigid in the desired shape, matching the shape of the bone. The locking shaft can also be placed into a transfer sleeve prior to insert into the rod 100. The transfer shaft, known in the art, aligns the rollers 410 and spacers 420, making insertion easier. As known, the transfer shaft is removed prior to rotation of the attachment end 405.

Figure 26:
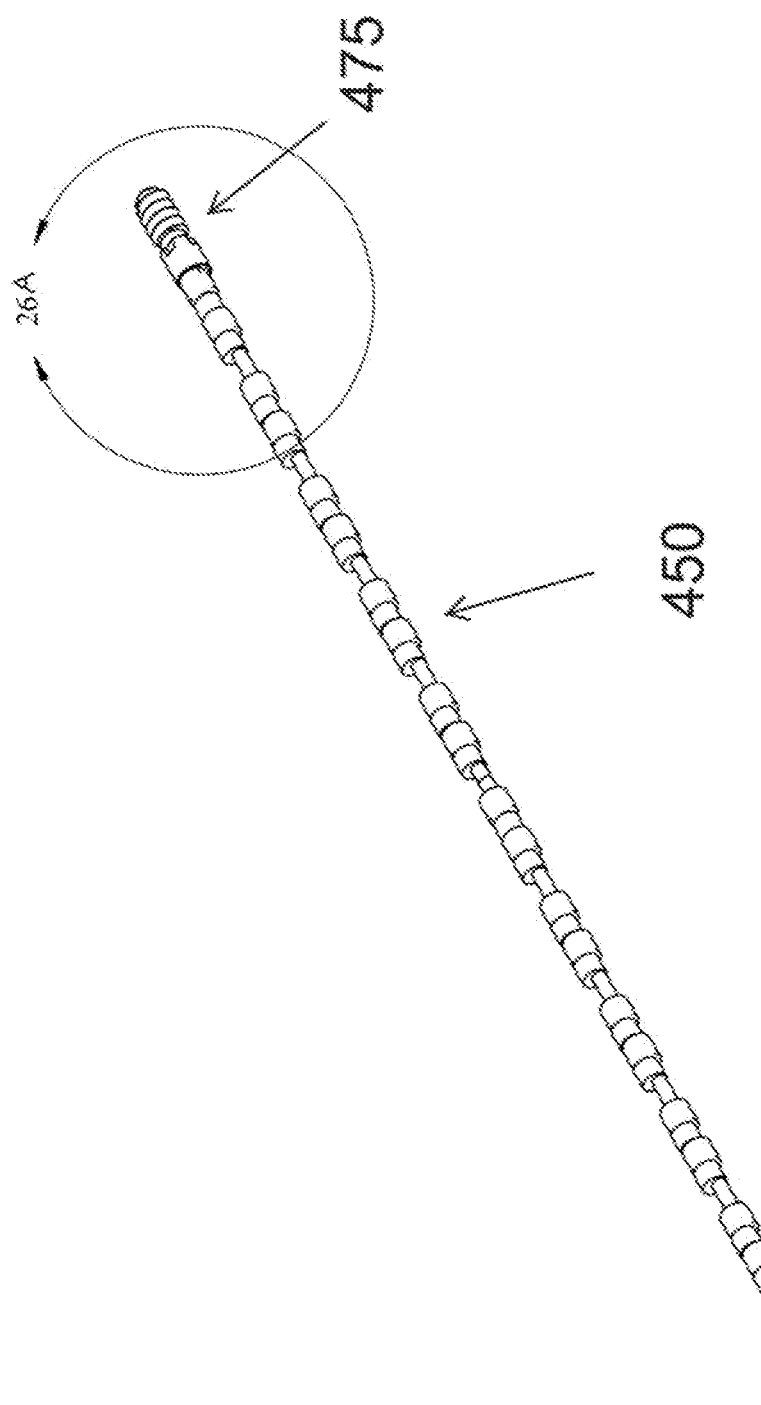
FIG. 26 is a perspective view of the locking shaft with a threaded leading end segment in accordance with the invention.
Figure 27:
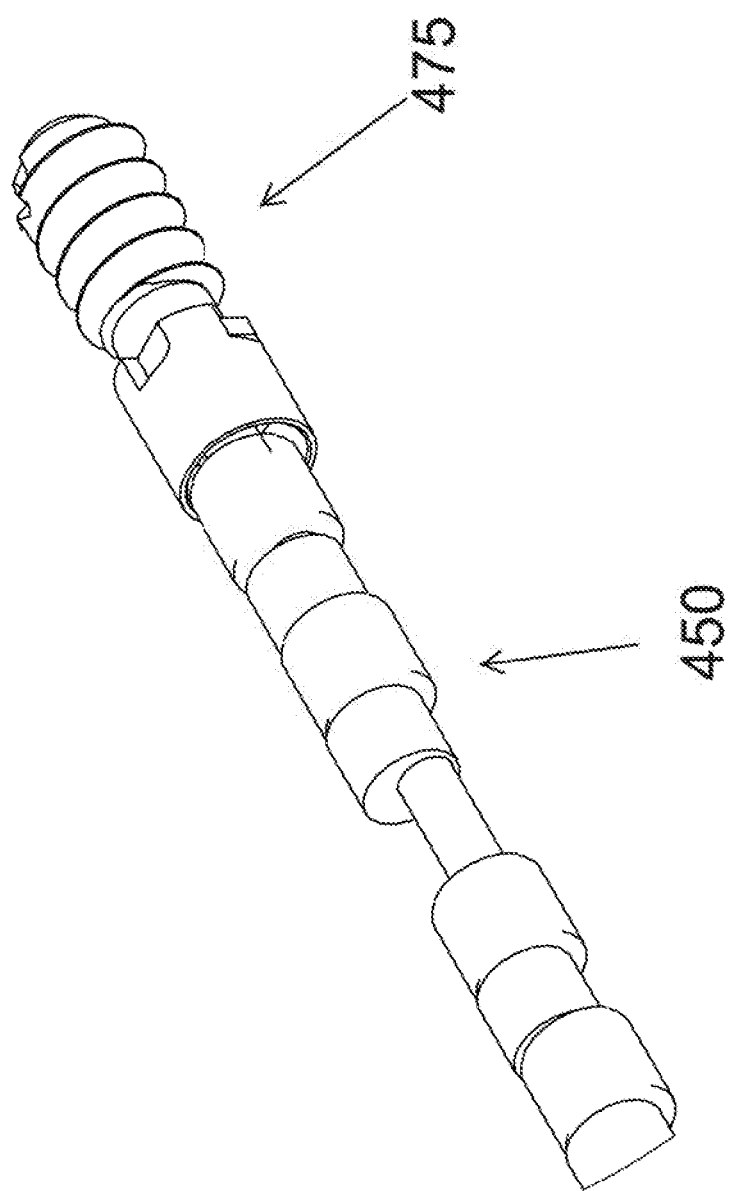
FIG. 27 is perspective view of the region of the locking shaft designated in FIG. 26 as 26A in accordance with the invention.

In another embodiment, the locking shaft 450 can have a threaded leading end segment 475, as illustrated in FIG. 26, at the distal end. The locking shaft 450 is inserted prior to the flexible rod 100 insertion which is inserted over the locking shaft 450. The enlarged view of 37A is illustrated in FIG. 27.

Preferably, the flexible segments as disclosed herein are formed by laser cutting an elongated tubular member of substantial wall thickness, to form the slot, or slots, around and along the tubular member in a helical manner. The disclosed rod uses a modification of the flexible shaft technology as taught by Krause et al in U.S. Pat. Nos. 6,053,922 and 6,447,518 and pending application U.S. Ser. No. 12/712,174 by imparting a serpentine or sinuous, helical slot along a segment or segments of the component. A serpentine or sinuous path can also be superimposed on a circumferential slot about the circumference of the shaft in the form of a generally sinusoidal wave. The sinusoidal wave forms dovetail-like teeth, which have a narrow base region and an anterior region that is wider than the base region, interlocking adjacent teeth. This sinuous path provides interlocking recesses and appendages to provide torsional and axial limitations to bending of the rod.

The teeth can have a configuration as illustrated in U.S. Pat. Nos. 4,328,839, and 6,053,922 the disclosure of which is incorporated herein by reference, as though recited in detail.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (e.g., of aspects across various embodiments), adaptations and/or alterations as would be appreciated by those in the art based on the present disclosure. The limitations in the claims (e.g., including that to be later added) are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function r step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language of the present invention or inventions should not be improperly interpreted as an identification of criticality, should not be improperly interpreted as applying across all aspects or embodiments (i.e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example."

While in the foregoing we have disclosed embodiments of the invention in considerable detail, it will understood by those skilled in the art that many of these details may be varied without departing from the spirit and scope of the invention.

What is claimed is:

1. A flexible connecting rod system for connection of two structures, said rod manufactured from a rigid material having a substantially cylindrical hollow body, said hollow body comprising:

an exterior diameter;
an interior core;
a leading segment having a securing area;
a trailing segment having a securing area;
a body between said leading segment and said trailing segment, said body having a leading edge adjacent said leading segment and a trailing edge adjacent said trailing segment;
at least two slots, each of said at least two slots having a proximal end and a distal end and following a sinuous, serpentine path to form a plurality of interlocking teeth, each of said at least two slots having a predetermined configuration, each of said predetermined configuration being determined by a combination comprising:
an individual pattern, said individual pattern being selected from the group comprising a helical pattern and a concentric pattern;
placement along said body with respect to said leading edge, said trailing edge and another of said at least two slots;
a pitch;
a helical angle, said helical angle being in the range of about 5 degrees to about 45 degrees;
an amplitude;
a slot cycle frequency; and
a width, said width forming an unbound joint permitting limited movement in any direction upon application of at least one from the group comprising: tensile, compressive, and torsion force;

wherein the predetermined configuration of each of said at least two slots individually in combination determines the flexibility of said flexible connecting rod thereby enabling the connection of structures selected from the group of rigid, flexible, semi-flexible and misaligned; and further comprising a locking shaft, said locking shaft comprising:
  a. a bar, said bar being flexible;
  b. multiple roller sets each of said multiple roller sets comprising at least a pair of rollers and spacers and having an outer diameter dimensioned to be received in said flexible connecting rod, said roller sets having a receiving hole, said receiving hole being offset from center and dimensioned to receive said bar;
wherein said bar and said multiple roller sets are dimensioned to fit within said flexible connecting rod and rotation of said bar rotates said multiple roller sets to wedge against the interior core of said flexible connecting rod.

2. The flexible connecting rod system of claim 1 wherein said individual pattern is multiple concentric slots.

3. The flexible connecting rod system of claim 1 wherein said proximal end of one of said at least two slots is spaced from said trailing edge and said distal end of another of said at least two slots is spaced from said leading edge.

4. The flexible connecting rod system of claim 1 wherein said proximal end of one of said at least two slots is spaced from said distal end of a subsequent slot leaving an unslotted section.

5. The flexible connecting rod system of claim 1 wherein said proximal end of one of said at least two slots is adjacent to said distal end of a subsequent slot.

6. The flexible connecting rod system of claim 1 wherein said securing area of said leading segment further comprises at least one securing member selected from at least one from the group comprising securing slots, holes, threads, deployable fins, talons, expandable cages, and cement.

7. The flexible connecting rod system of claim 1 wherein said securing area of said trailing segment further comprises at least one securing member selected from at least one of the group comprising securing slots, holes, threads, deployable fins, talons, expandable cages, and cement.

8. The flexible connecting rod system of claim 1 wherein each of said at least two slots has an increased width in a first direction compared to a second direction to provide increased flexibility in said first direction.

9. The flexible connecting rod system of claim 1 wherein each of said at least two slots has a width between about 0.5% and about 15.0% of the diameter of said flexible connecting rod and a maximum of about 20.0% to 25.0% of said diameter of said flexible connecting rod.

10. The flexible connecting rod system of claim 1 wherein a ratio of said amplitude of said path to said pitch of each of said at least two slots is in the range from greater than 0.1 to about 0.8.

11. The flexible connecting rod system of claim 1 further comprising an elastomeric material, said elastomeric material interacting with said flexible connecting rod from at least one of the group comprising:
  a. at least one of said at least one slot being filled;
  b. at least one portion of said interior core adjacent to said at least one flexible center section being filled;
  c. said interior core being filled;
  d. elastomeric material extending through and filling, said at least one slot;
  e. elastomeric material encompassing at least a portion of said exterior diameter;
  f. elastomeric material encompassing said exterior diameter, filling and extending through said at least one slot;
  g. elastomeric material encompassing at least a portion of said exterior diameter of said flexible connecting rod.

12. The flexible connecting rod system of claim 1 wherein said slot cycle frequency of said helical pattern about 0.25 to about 5 cycles per diameter length.

13. The flexible connecting rod system of claim 1 wherein either said spacers are non-rotatably affixed to said bar and said rollers are rotatable on said bar or said spacers and said rollers are non-rotatably affixed to said bar.

* * * * *